United States Patent [19]

Martin

[11] 4,368,188

[45] Jan. 11, 1983

[54] COSMETIC TONER FORMULATION

[75] Inventor: Joe O. Martin, Martinsville, Ind.

[73] Assignee: Eli Lilly and Company, Indianapolis, Ind.

[21] Appl. No.: 289,656

[22] Filed: Aug. 3, 1981

[51] Int. Cl.³ .................... A61K 31/78; A61K 47/00
[52] U.S. Cl. ................................ 424/81; 424/362; 424/365
[58] Field of Search .................. 424/358, 365, 81

[56] References Cited

U.S. PATENT DOCUMENTS

| | | | |
|---|---|---|---|
| 3,924,004 | 12/1975 | Chang | 424/358 |
| 4,268,502 | 5/1981 | Martin | 424/83 |
| 4,272,544 | 6/1981 | Cella et al. | 424/273 |

OTHER PUBLICATIONS

Harry, The Principles & Practice of Modern Cosmetics, vol. II, 1963, pp. 16 & 17.
Harry, The Principles & Practice of Modern Cosmetics, vol. I, 1963, pp. 140 to 144.
Ash, A Formulary of Cosmetic Preparations, 1977, pp. 255 to 259.

*Primary Examiner*—Dale R. Ore
*Attorney, Agent, or Firm*—Karen B. O'Connor; Arthur R. Whale

[57] ABSTRACT

A novel cosmetic skin toner formulation is described which is non-irritating and non-stinging.

1 Claim, No Drawings

COSMETIC TONER FORMULATION

This invention relates to a novel cosmetic toner formulation, which is non-irritating and non-stinging.

It is, therefore, an object of the present invention to provide a cosmetic toner formulation. The toner can be used in conjunction with other cosmetic formulations.

The toner formulation is one of a four-component regime, which is used to treat sensitive skin. The other three components are: a cleanser, a moisturizer, and a cream. Each of the other three components is a separate invention; the cleanser is claimed in application Ser. No. 289,657, filed Aug. 3, 1981; the moisturizer is claimed in application Ser. No. 289,655, filed Aug. 3, 1981; and the cream is claimed in application Ser. No. 289,653, Aug. 3, 1981. The method of treating sensitive skin using the regime is claimed in application Ser. No. 289,658, filed Aug. 3, 1981. In addition, a cream pack formulation is claimed in application Ser. No. 289,654, filed Aug. 3, 1981.

The toner formulation consists essentially of, in percent by weight:

| Ingredients | Percent |
| --- | --- |
| polyacrylic acid polymer (Carbopol No. 941) | 0.10 |
| glycerin | 2.00 |
| glyoxyldiureide | 0.30 |
| acetylated polyoxyethylene (10) lanolin alcohol | 1.00 |
| cetyl/stearyl 2-ethylhexanoate | 1.00 |
| 98% triethanolamine | 0.10 |
| preservative | q.s. |
| deionized water | q.s. to 100% |

One skilled in the cosmetic formulation art will appreciate that various preservatives can be added to the formulation in sufficient quantities. These preservatives include the esters of p-hydroxybenzoic acid, such as methyl p-hydroxybenzoate, and propyl p-hydroxybenzoate; cis-1-(3-chloroally)-3,5,7-triaza-1-azoniaadamantane chloride; ethylenediaminetetraacetic acid (EDTA) and salts of EDTA; imidazolidinyl urea; and the like or any combination thereof. The total amount of preservative used can vary, but usually it is from about 0.3 to about 1.0 percent.

In addition, color and essence can be included in the formulation as desired. Color additives would include both natural and artificial dyes, such as carotenoid derivatives, D+C or F,D+C colors, and the like, while essences can include any non-irritating natural and artificial oils, perfumes, and the like.

The formulation is both non-irritating and non-stinging, according to standard cosmetic testing procedures. The first procedure utilized was the Lanman-Maibach Cumulative Irritation Test, which is a 21-day patch irritation procedure as described by Dr. B. M. Lanman at the Joint Conference on Cosmetic Sciences, Apr. 21–23, 1968 Washington D.C. as further modified in Phillips, L., Steinberg M., Maibach, H., and Akers, W., *Toxicology and Applied Pharmacology*, 21, 369-382 (1972). The non-stinging properties of the formulation were established by the Lactic Acid Sting Test as described in P. J. Frosch and A. M. Kligman: "A Method for Appraising the Stinging Capacity of Topically Applied Substances" *Journal of the Society of Cosmetic Chemists* 28, 197-209, May 1977.

In general, the individual ingredients used in the formulation should be of a quality or purity (such as U.S.P. or N.F.) suitable for cosmetic use.

The formulation is prepared by mixing the ingredients according to conventional methods and the preparation of this formulation is described in the following example. The example is illustrative of the formulation, but is not to be construed as limiting the invention.

EXAMPLE

Toner Formulation:

| Phase | Ingredient | Percent by weight |
| --- | --- | --- |
| A | deionized water | 10.00 |
|   | Carbopol No. 941 (B. F. Goodrich, polyacrylic acid polymer) | 0.10* |
| B | deionized water | 82.90 |
|   | glycerin | 2.00 |
|   | methylparaben (methyl p-hydroxybenzoate) | 0.20 |
|   | Allantoin (Sutton and Schuylkill, glyoxyldiureide) | 0.30 |
|   | imidazolidinyl urea | 0.30 |
| C | acetylated polyoxyethylene (10) lanolin alcohol | 1.00 |
|   | Pur-Cellin Oil (Dragoco, cetyl/stearyl 2-ethylhexanoate) | 1.00 |
|   | propylparaben (propyl p-hydroxybenzoate) | 0.10 |
| D | deionized water | 2.00 |
|   | 98% triethanolamine | 0.10 |

*Concentration may be increased up to 0.15% to achieve viscosity specification.

Procedure:

Phase A is prepared one day before the batch manufacture. The Carbopol is added very slowly to the deionized water while mixing vigorously. The mixing is continued until all the Carbopol is wetted. Then Phase A is mixed again before being added to Phase B.

The ingredients of Phase B are blended and then heated to about 70°–75° C. Phase B is mixed with simple agitation (i.e. propeller mixer) until all the powders are dissolved. Phase A is added to Phase B and mixed until uniform. The temperature is maintained at about 70°–75° C.

The ingredients of Phase C are blended and then heated to about 70°–75° C. The mixing continues until all the propylparaben is dissolved. (Phase C has a turbid-hazy appearance and must be kept under agitation.)

Phase C is added to Phase AB and mixed for a few minutes with simple agitation. Phase ABC is then cooled to about 45°–50° C. while mixing. Phase D is prepared by mixing the triethanolamine into the deionized water, and then Phase D is added to Phase ABC. Phase ABCD is mixed and cooled to about 30°–35° C.

I claim:

1. A cosmetic toner formulation consisting essentially of, in percent by weight:

| Ingredients | Percent |
| --- | --- |
| polyacrylic acid polymer (Carbopol No. 941) | 0.10 |
| glycerin | 2.00 |
| glyoxyldiureide | 0.30 |
| acetylated polyoxyethylene (10) lanolin alcohol | 1.00 |
| cetyl/stearyl 2-ethylhexanoate | 1.00 |
| 98% triethanolamine | 0.10 |
| preservative | q.s. |
| deionized water | q.s. to 100% |

* * * * *